United States Patent
Miyamoto et al.

(10) Patent No.: US 6,692,760 B2
(45) Date of Patent: Feb. 17, 2004

(54) POLYMERIC MATERIAL FOR ARTIFICIAL BONE

(75) Inventors: Takeaki Miyamoto, Kyoto (JP); Tadashi Kokubo, Kyoto (JP)

(73) Assignee: Japan Science and Technology Corporation, Saitama (JP)

(*) Notice: Subject to any disclaimer, the term of this patent is extended or adjusted under 35 U.S.C. 154(b) by 4 days.

(21) Appl. No.: 09/964,688

(22) Filed: Sep. 28, 2001

(65) Prior Publication Data

US 2002/0031540 A1 Mar. 14, 2002

Related U.S. Application Data

(62) Division of application No. 09/530,800, filed as application No. PCT/JP99/04791 on Sep. 3, 1999.

(30) Foreign Application Priority Data

Sep. 6, 1998 (JP) .............................. 10-269010

(51) Int. Cl.⁷ .......................... A61F 2/00; A61F 13/00; A61F 9/14; A61F 2/28; A61F 2/36
(52) U.S. Cl. .................. 424/423; 424/422; 424/488; 514/23; 514/54; 623/16.11; 623/23.61
(58) Field of Search .................. 424/488, 422, 424/423; 514/23, 54; 623/16.11, 23.61

(56) References Cited

U.S. PATENT DOCUMENTS 5,770,229 A * 6/1998 Tanihara et al. ............ 424/488
5,830,493 A 11/1998 Yokota et al.
5,990,381 A 11/1999 Nishihara

OTHER PUBLICATIONS

WPI, Derwent accession No. 1982–02695, abstract (JP 56149389).*
WPI, Derwent accession No. 1988–208078, abstract (JP 63143071).*
WPI, Derwent accession No. 1990–071210, abstract (JP 02023976).*

* cited by examiner

Primary Examiner—Thurman K. Page
Assistant Examiner—Blessing Fubara
(74) Attorney, Agent, or Firm—Wenderoth, Lind & Ponack, LLP

(57) ABSTRACT

A novel polymeric material for artificial bones, comprising a solid or gel-form base containing, as the main component, either a polysaccharide having carboxyl groups or their derivatives, or a polysaccharide having carboxyl groups or their derivatives, introduced into it, which also has calcium ions bonded thereto, and shows excellent ability to form apatite.

26 Claims, 3 Drawing Sheets

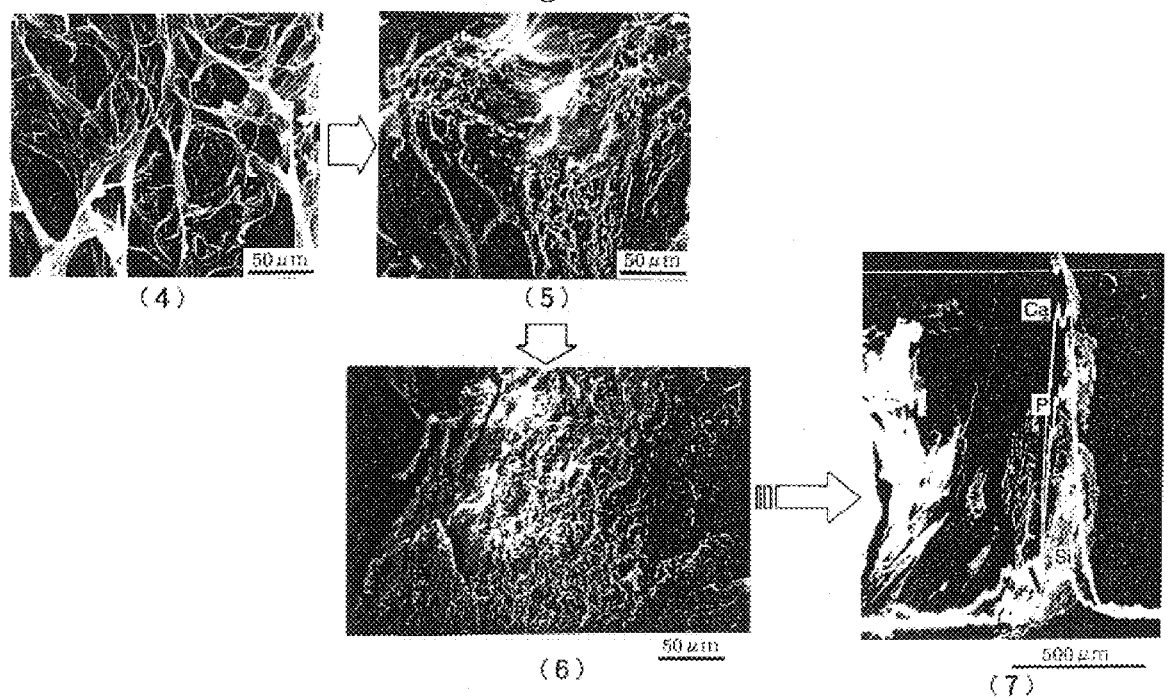

POLYMERIC MATERIAL FOR ARTIFICIAL BONE

This is a divisional of Ser. No. 09/530,800, filed May 5, 2000, which is a 371 of PCT/JP99/04791, filed Sep. 3, 1999.

TECHNICAL FIELD

The present application relates to a polymeric material for artificial bones. More specifically, the present application relates to a novel polymeric material for artificial bones which can effectively form an apatite layer similar to that of bones in a simulated body fluid.

BACKGROUND OF THE INVENTION

It has been known that the bone is a composite with a thee-dimensional structure formed exquisitely from fine crystals of apatite, an inorganic substance, deposited on fibers of collagen, an organic substance. Various approaches have been studied thus far for finding a method to artificially build a similar structure.

However, all such methods employ aqueous solutions with very high concentrations of ions, as compared with the ion concentrations of body fluid, for forming an apatite layer. Such aqueous solutions can only form apatite layers differing greatly in structure and composition from those of bones in a living body, and the materials obtained therefrom cannot be readily joined with living bones.

Under these circumstances, we, the inventors of the present invention, have discovered the usefulness of a method imitating in vivo reactions (a biomimetic method), and have devoted ourselves to the search for a method to deposit apatite on an organic polymer base. However, we had not been able to find any polymeric material thus far that could be used to effectively deposit a large amount of apatite with structure and tissue close to those of the inorganic substance in bones.

For example, we experimented with the use of cellulose base as the organic polymer, taking in consideration its hydrophilic property and the reactivity of the OH group, and tried to form an apatite layer in a simulated body fluid by introducing onto the surface of the base a silanol (Si—OH) group known for being effective in the nucleation of apatite. However, we have found that the apatite layer formation was too slow for this method to be effective.

The object of the present invention is, therefore, to overcome the above problems and to provide a novel polymeric material for artificial bones, which can more effectively form an apatite layer in a simulated body fluid, with structure and composition showing mechanical properties similar to those of bones.

DISCLOSURE OF THE INVENTION

To attain the above object, provided as the first embodiment is a polymeric material for artificial bones, comprising a solid or gel-form base containing, as its main component, a polysaccharide containing carboxyl groups or their derivatives, or a polysaccharide having carboxyl groups or their derivatives introduced to it, and has calcium ions bonded thereto.

Provided as the second embodiment is a polymeric material for artificial bones, in which the solid base is in the form of a porous solid, fiber, film, or bulk. Provided as the third embodiment is a polymeric material for artificial bones in which the polysaccharide is a natural polysaccharide containing carboxyl groups, or a polysaccharide derivative having carboxyl groups introduced to it.

Also, as the fourth embodiment, a polymeric material for artificial bones, on which an apatite layer can form in a simulated body fluid, is provided, and as the fifth embodiment, a method of manufacturing a polymeric material for artificial bones of the above embodiments comprising the contact of a solid or gel-form base containing, as its main component, a polysaccharide containing carboxyl groups or their derivatives, or a polysaccharide having carboxyl groups or their derivatives introduced into it, with a solution containing calcium ions, to crosslink the said carboxyl groups or their derivatives. Furthermore, as the sixth embodiment, an artificial bone structure comprising a polymeric material for artificial bones as above, with an apatite layer formed on its surface, is provided.

BRIEF DESCRIPTION OF THE DRAWINGS

FIG. 3 is a drawing submitted for the SEM and SEM-EDX photographs of sample N, exemplifying the present invention. (4) shows a CMC gel, (5) shows the gel of (4) after TEOS treatment, (6) shows (5) immersed in 1.0 SBF for two weeks, and (7) is a drawing based on the SEM-EDX photograph of (6) which shows it in lower magnification.

BEST MODE FOR CARRYING OUT THE INVENTION

Figure 1:
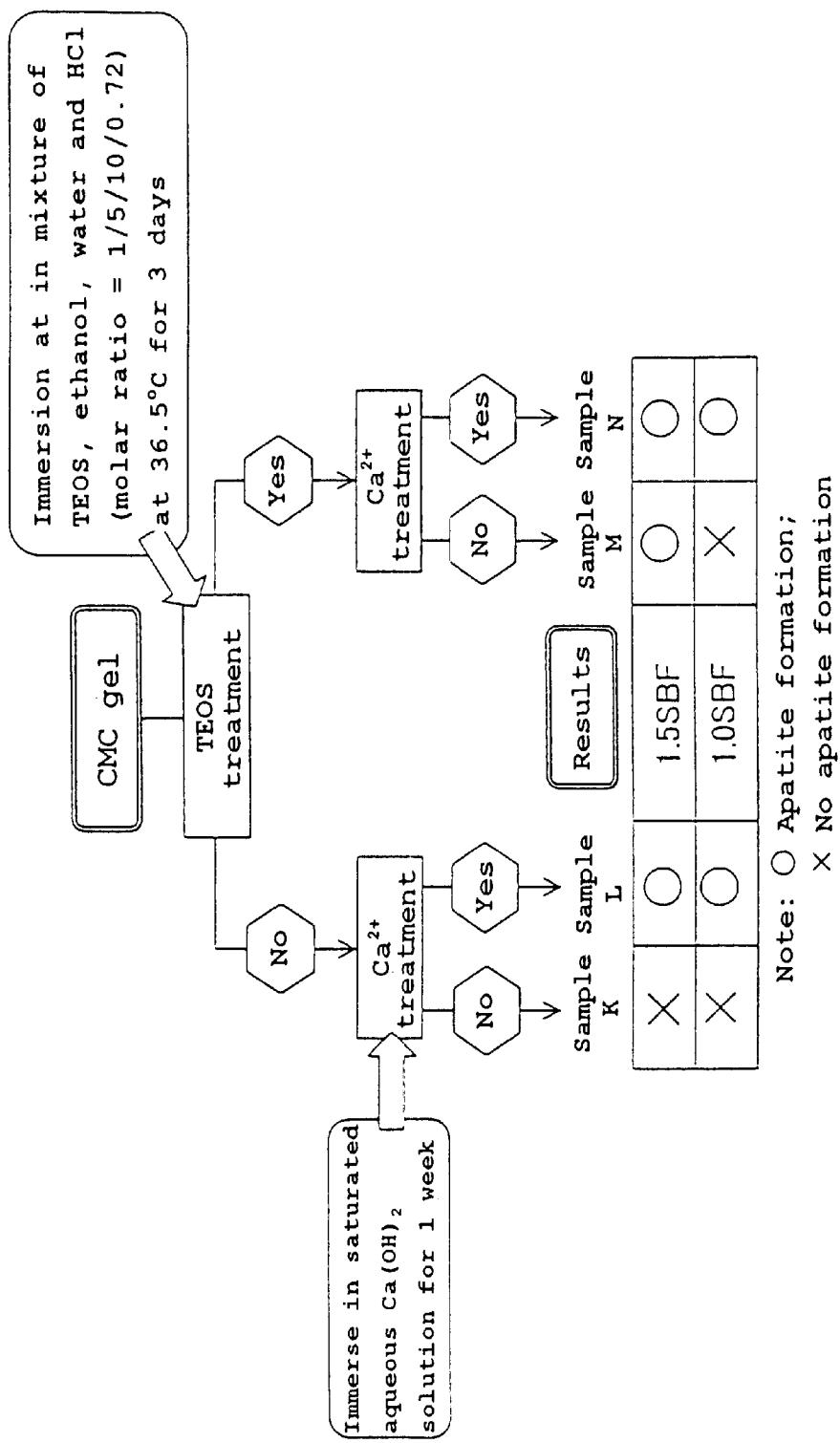
FIG. 1 is a diagram showing a process that exemplifies the present invention, with the results of apatite formation.

The invention of the present application indicated above is described in further detail.

The polymeric material for artificial bones according to the invention of the present application contains, as stated before, a polysaccharide solid or gel-form base as its main component, and has calcium ions bonded thereto, where the polysaccharide composing the polymeric material has carboxyl groups or their derivatives, or has such groups introduced to it. Such derivatives are defined as various groups obtained by replacing the hydrogen atom of carboxyl groups (—COOH) to give, for example, —COOR (ester) or —COOM (a salt in which M is a metal atom), which do not hinder the bonding of calcium ions ($Ca^{2+}$), but rather contribute to it. Examples include esters or salts which can readily form —CO—O— in the presence of water. They may also be a type of derivative which works as a protective group capable of forming —CO—O— when calcium ions are bonded to the polysaccharide.

The polysaccharide may contain carboxyl groups or their derivatives within its own molecular structure, or have such groups introduced therein by chemical reactions.

The polysaccharide which is the main component of the polymeric material for artificial bones according to the present invention may be any natural or synthetic substance, but is preferably a cellulose-type or chitin-type polysaccharide, due to their ease in obtaining and handling, and their high structural strength and stability. Needless to say, other polysaccharides may also be used.

Specific examples of the polysaccharides include carboxymethyl cellulose (CMC), carboxylcellulose and carboxymethyl chitin.

The solid base for the polymeric material for artificial bones may be in any of the various forms available, including fibers, bulk and film.

The bonding of calcium ions to the solid or gel-form base may be carried out by, for example, allowing it to come into contact with a solution containing calcium ions. Such contact may be carried out by soaking the solid or gel-form base in an aqueous solution of calcium ions ($Ca^{2+}$), or more specifically of $Ca(OH)_2$.

The bonding of calcium ions to the base is first considered as the bonding of calcium ions with the carboxyl groups. In other words, a divalent calcium ion combines with two univalent carboxyl groups, thereby functioning as a crosslinking group for the two carboxyl groups. Therefore, it is desirable that the bonding of calcium ions be carried out as close to saturation as possible. The physical adsorption of calcium ions to the polymer material for artificial bones is also taken into consideration.

The polymeric material for artificial bones according to the present invention forms apatite with structure and composition similar to those of bones on its surface, when coming in contact with human body fluid. The formation of the apatite layers is far more efficient than formerly known methods. According to the present invention, a method for forming an artificial bone structure, as described above, is also provided.

Thus provided, according to the present invention, is a polymeric material for artificial bones, on which an apatite layer is formed in a simulated body fluid. An example of such simulated body fluid is SBF [T. Kokubo, H. Kushitani, S. Sakka, T. Kitsugi and T. Yamamuro: "Solutions able to reproduce in vivo surface-structure changes in bioactive glass-ceramic A-W", *J. Biomed. Mater.*, Res. 24, 721–734 (1996)]. SBF is an aqueous solution with ion concentrations approximately equal to those of human body fluid, as shown below.

TABLE 1

|  | Concentration of ions (in mM) |
| --- | --- |
| $Na^+$ | 142 |
| $K^+$ | 5.0 |
| $Mg^{2+}$ | 1.5 |
| $Ca^{2+}$ | 2.5 |
| $Cl^-$ | 148 |
| $HCO_3^-$ | 4.2 |
| $HPO_4^{2-}$ | 1.0 |
| $SO_4^{2-}$ | 0.5 |

The polymeric material for artificial bones according to the present invention as described so far forms hydroxyapatite, $Ca_{10}(PO_2)_6(OH)_2$, in a simulated body fluid, and can be used as artificial bones in various areas of the body, such as artificial vertebrae, artificial intervertebral disk, artificial ilium, artificial neck bone, and artificial skull.

The invention will now be described in further detail based on the following examples.

EXAMPLES

A commercially available product of CMC (carboxymethyl cellulose) was chosen as cellulose having —COOH and —COONa groups (D.S.=0.7), and was gelated according to literature: U. Anbergen and W. Oppormann, *Polymer*, 31, 1854 (1990). The gel was treated through various processes as shown in FIG. 1, and the process of apatite formation in 1.0 SBF and 1.5 SBF were evaluated by SEM (scanning electron microscope) and energy dispersion X-ray spectroscopy (EOX).

Here, SBF is an aqueous solution having ionic concentrations approximately equal to those of human body fluid, as described before.

The TEOS (tetraethoxysilane) treatment of the gel was carried out by immersing it in a mixture of TEOS, ethanol, water and 1N-HCl (molar ratio=1/10/5/0.72), at 36.5° C. for three days.

The $Ca^{2+}$ treatment of the gel was carried out by immersing it in a saturated aqueous solution of $Ca(OH)_2$ for a week.

FIG. 1 also shows the results of apatite formation.

From these results, the following was observed:

(i) Apatite can not nucleate with carboxyl groups alone (Sample K).

(ii) Even after TEOS treatment, without $Ca^{2+}$ treatment, apatite can only be formed in 1.5 SBF (Sample M).

(iii) Samples of CMC treated with $Ca^{2+}$ show apatite nucleation in 1.0 SBF, with or without TEOS treatment, and show very rapid formation of apatite (Samples L and N).

Figure 2:
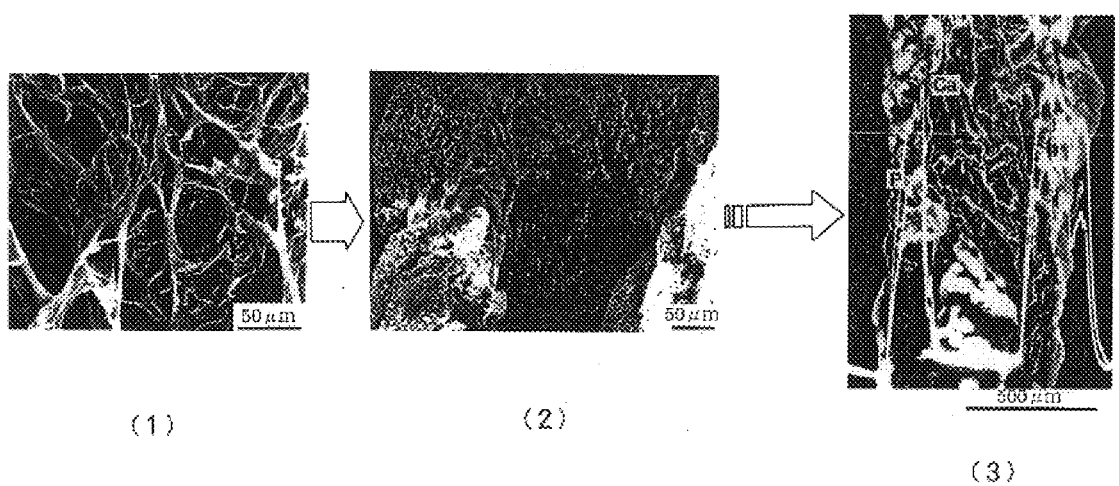
FIG. 2 is a drawing submitted for the SEM and SEM-EDX photographs of sample L, exemplifying the present invention. (1) shows a CMC gel, (2) shows the gel of (1) soaked in 1.0 SBF for two weeks, and (3) is a drawing submitted for the SEM-EDX photograph of (2) which shows it in lower magnification.

FIG. 2 is a drawing based on the SEM and SEM-EDX photographs of Sample L, and FIG. 3 is a drawing based on the SEM and SEM-EDX photographs of Sample N.

From the above results, it can be concluded that $Ca^{2+}$ has a higher apatite nucleation ability than Si—OH groups, and that polysaccharides with carboxyl groups exhibit a high apatite nucleation ability when bonded with $Ca^{2+}$.

Industrial Applicability

According to the invention of the present application, a novel polymeric material for artificial bones which can form apatite efficiently in a way similar to in vivo reaction, as described in detail above, is provided.

What is claimed is:

1. A polymeric material for artificial bone, comprising a solid substrate consisting of a polysaccharide which contains carboxyl groups, wherein said carboxyl groups are linked in pairs by one calcium atom.

2. The polymeric material for artificial bone of claim 1, wherein the solid substrate is porous.

3. The polymeric material for artificial bone of claim 1, wherein the solid substrate is non-porous.

4. The polymeric material for artificial bone of claim 1, wherein the solid substrate is in the form of a bulk, fiber or film.

5. The polymeric material for artificial bone of claims 1, 2, 3 or 4 wherein the polysaccharide is selected from natural polysaccharides containing carboxyl groups, or modified polysaccharides in which carboxyl groups are introduced.

6. The polymeric material for artificial bone of claims 1, 2, 3 or 4, wherein the polysaccharide is carboxymethylcellulose.

7. A polymeric material for artificial bone, comprising a non-ionically crosslinked gel substrate containing a polysaccharide which contains carboxyl groups, wherein said carboxyl groups are linked in pairs by one calcium atom.

8. The polymeric material for artificial bone of claim 7, wherein the polysaccharide is selected from natural polysaccharides containing carboxyl groups, or modified polysaccharides in which carboxyl groups are introduced.

9. The polymeric material for artificial bone of claim 7, wherein the polysaccharide is carboxymethylcellulose.

10. A method for producing polymeric material for artificial bone, comprising:

(a) the gelation of a solid substrate using a non-ionic water-soluble crosslinking agent to cross-link the polysaccharide in the solid substrate; and (b) the submergence of the gelated substrate to a solution containing calcium ions.

11. The method for producing polymeric material for artificial bone of claim 10, wherein the non-ionic water-soluble crosslinking agent is selected from the group consisting of water-soluble aldehides, epoxides and vinyl compounds.

12. A method for producing the polymeric material for artificial bone, comprising the submergence of a non-ionically crosslinked gel substrate in a solution containing calcium ions.

13. The method for producing polymeric material for artificial bone of claims 10, 11 or 12, wherein the polysaccharide is selected from natural polysaccharides containing carboxyl groups, or modified polysaccharides in which carboxyl groups are introduced.

14. The method for producing polymeric material for artificial bone of claims 10, 11 or 12, wherein the polysaccharide is carboxymethylcellulose.

15. A method for manufacturing an artificial bone structure, comprising the submergence of the polymeric material of claim 1 in body fluid or a solution containing ion concentrations similar to that of body fluid.

16. A method for manufacturing an artificial bone structure, comprising the submergence of the polymeric material of claim 2 in body fluid or a solution containing ion concentrations similar to that of body fluid.

17. A method for manufacturing an artificial bone structure, comprising the submergence of the polymeric material of claim 3 in body fluid or a solution containing ion concentrations similar to that of body fluid.

18. A method for manufacturing an artificial bone structure, comprising the submergence of the polymeric material of claim 4 in body fluid or a solution containing ion concentrations similar to that of body fluid.

19. A method for manufacturing an artificial bone structure, comprising the submergence of the polymeric material of claim 5 in body fluid or a solution containing ion concentrations similar to that of body fluid.

20. A method for an artificial bone structure, comprising the submergence of the polymeric material of claim 6 in body fluid or a solution containing ion concentrations similar to that of body fluid.

21. A method for manufacturing an artificial bone structure, comprising the submergence of the polymeric material of claim 7 in body fluid or a solution containing ion concentrations similar to that of body fluid.

22. A method for manufacturing an artificial bone structure, comprising the submergence of the polymeric material of claim 8 in body fluid or a solution containing ion concentrations similar to that of body fluid.

23. A method for manufacturing an artificial bone structure, comprising the submergence of the polymeric material of claim 9 in body fluid or a solution containing ion concentrations similar to that of body fluid.

24. An artificial bone structure formed by the method of claims 15, 16, 17, 18, 21, 22, 23, comprising an apatite layer similar to that of bone bonded to the surface of the polymeric material through calcium.

25. An artificial bone structure formed by the method of claim 19, comprising an apatite layer similar to that of bone bonded to the surface of the polymeric material through calcium.

26. An artificial bone structure formed by the method of claim 20, comprising an apatite layer similar to that of bone bonded to the surface of the polymeric material through calcium.

* * * * *